United States Patent [19]

Pieniak et al.

[11] Patent Number: 5,098,423
[45] Date of Patent: Mar. 24, 1992

[54] LOW BULK DISPOSABLE DIAPER

[75] Inventors: Heinz A. Pieniak, Des Moines; Gloria Huffman, Federal Way, both of Wash.

[73] Assignee: McNeil-PPC, Inc., Milltown, N.J.

[21] Appl. No.: 596,756

[22] Filed: Oct. 31, 1990

Related U.S. Application Data

[63] Continuation of Ser. No. 263,529, Oct. 27, 1988, abandoned.

[51] Int. Cl.⁵ .............................................. A61F 13/15
[52] U.S. Cl. ................................ 604/385.1; 604/372; 604/385.2
[58] Field of Search ................... 604/372, 385.1, 385.2

[56] References Cited

U.S. PATENT DOCUMENTS

| | | |
|---|---|---|
| 3,860,003 | 1/1975 | Buell . |
| 3,938,522 | 2/1976 | Repke ............................ 604/372 |
| 4,559,050 | 12/1985 | Iskra . |
| 4,560,372 | 12/1985 | Pieniak . |
| 4,573,988 | 3/1986 | Pieniak et al. . |
| 4,596,567 | 6/1986 | Iskra . |
| 4,605,402 | 8/1986 | Iskra . |
| 4,676,784 | 6/1987 | Erdman et al. . |
| 4,738,676 | 4/1988 | Osborn ............................ 604/385.1 |
| 4,838,885 | 6/1989 | Bernardin ........................ 604/385.1 |

Primary Examiner—Robert Bahr
Assistant Examiner—Karen A. Richard
Attorney, Agent, or Firm—Dressler, Goldsmith, Shore, Sutker & Milnamow, Ltd.

[57] ABSTRACT

A disposable diaper is particularly configured for improved fit and comfort, as well as provide enhanced absorptive capacity and leakage-resistant characteristics. Improved fit and comfort are achieved by providing the diaper with a relatively thin, narrow absorbent panel, with the panel configured to provide desirably high absorbency efficiency for enhanced performance characteristics. Additionally, the diaper is provided with elasticized leg openings each including a plurality of elastic members. The innermost ones of the elastic members are positioned relatively close together, thereby providing improved fit.

17 Claims, 3 Drawing Sheets

LOW BULK DISPOSABLE DIAPER

This application is a continuation of application Ser. No. 07/263,529, filed Oct. 27, 1988 now abandoned.

TECHNICAL FIELD

The present invention relates generally to disposable absorbent articles including diapers and incontinent products, and more particularly to a low bulk disposable diaper configured for improved fit and comfort while exhibiting enhanced absorptive and leakage-resistant characteristics.

BACKGROUND OF THE INVENTION

The use of disposable diapers for infant care has become increasingly widespread in recent years, with these disposable products providing substantial advantages and convenience over reuseable diapers. A typical disposable diaper structure includes a layer of liquid-retaining absorbent material sandwiched between a moisture pervious facing layer positioned adjacent the skin of the wearer, and a moisture impervious plastic backing sheet to confine moisture within the absorbent layer.

In the past, the absorbent layer has typically been comprised of batt of loosely compacted cellulosic fibers, usually comminuted wood pulp or "fluff". While such absorbent material is relatively inexpensive and is capable of quickly absorbing liquids, the typical diaper structure including such material is configured such that it detracts from the comfort of the wearer.

Specifically, typical disposable diaper products are relatively thick and exhibit high bulk. Such arrangements were thought to be desirable because consumers showed a preference for thicker diapers in view of their higher absorptive capacity and reduced tendency to leak. Even those products which include hydrocolloid or superabsorbent materials in combination with wood pulp are relatively thick.

The appearance of bulkiness of a diaper is related to the panel thickness and to the volume of the diaper absorbent panel. The volume of the panel affects the comfort of the product as felt by the wearer, typically infants, and also affects consumer preferences.

With regard to wearer comfort, testing has shown that a standing infant of five months of age or older, and weighing approximately 16 pounds and up, has only a very small distance between its upper thighs, typically 0.5 inches or less. As will be appreciated, whatever thickness a diaper exhibits between the infant's legs that is in excess of the child's natural crotch width will necessarily press against the child's thighs, spreading the thighs apart to accommodate the diaper. This unnatural displacement of the child's thighs encumbers the child's mobility, and is typically perceived as uncomfortable.

Further, consumers prefer a snug-fitting diaper not only because of its aesthetic appeal, but also because of the desired ease with which outer clothing can be fit over the diaper. It is therefore preferred that a diaper does not tend to hang low between an infant's legs with a bagging or pouch-like appearance. As will be appreciated, however, in order for the diaper to fit close to the body in the limited space between the thighs, the diaper must fold or corrugate. As a consequence of this multiplying effect of the diaper thickness, undesirable bulk is created in the crotch region which is larger than the natural space provided between the thighs, with the resultant decrease in comfort.

In view of the foregoing, it is desirable to provide a disposable diaper product which is configured to exhibit desirably low bulk for improved fit and comfort, while at the same time exhibiting enhanced absorptive capacity per unit volume of the absorbent diaper panel so that the diaper can be used effectively while minimizing leakage.

SUMMARY OF THE INVENTION

The disposable diaper embodying the principles of the present invention has been particularly configured for improved fit and comfort by providing a construction which exhibits relatively low bulkiness, while at the same time providing efficient absorbency so as to avoid leakage while in use. This is achieved by providing the diaper with an absorbent panel structure which is relatively thin and narrow, yet exhibits a high absorptive capacity per unit volume of the panel to obtain the desired characteristics. In particular, the structure is configured so as to minimize the unnatural outward displacement of an infant's thighs while wearing the product, thus enhancing comfort.

In accordance with the illustrated embodiment, the present disposable diaper includes an absorbent panel, with a moisture-pervious facing layer positioned in overlying relationship on one side of the absorbent panel. The facing layer is adapted for positioning adjacent the wearer of the diaper, and may typically comprise non-woven fabric or the like.

The diaper construction further includes a backing layer positioned on the side of the absorbent panel opposite the facing layer. While the backing layer may be formed from moisture-impervious plastic sheet material, the illustrated embodiment is configured such that a moisture-impervious barrier layer is provided in association with a moisture-pervious backing layer. The barrier layer has a surface area which is less than that of the backing layer, thereby minimizing the occlusion of the diaper for improved breathability, further enhancing comfort.

The absorbent panel of the present disposable diaper comprises a matrix of absorbent material, and includes an impact or target zone, defined as the second and third fifths of the panel length, measured from the front of the diaper. In achieving the desired comfort and performance characteristics, the present diaper is configured such that the minimum transverse dimension of the absorbent panel at the impact zone is no more than about 40 times the thickness dimension panel in this region. Additionally, the absorbent panel is configured so as to exhibit sufficient inherent absorbency to provide the impact zone with an absorbency efficiency index of at least 1.5. This absorbency efficiency index is determined by ascertaining the absorptive characteristics of a diaper's absorbent panel as it relates to the bulk of the panel. Comparison tests with numerous commercial products show that a diaper embodying the principles of the present invention exhibits a desirably high efficiency index.

In achieving the desired characteristics for the present diaper construction, the preferred absorbent matrix of the absorbent panel comprises superabsorbent material, preferably in combination with a fibrous web wherein the superabsorbent material comprises from about 200 to about 1500 percent, by dry weight basis, of the fibrous material in the web. In the preferred form, the fibrous material is in the form of a substantially high loft, resilient fibrous web layer, with the superabsorbent material distributed within the fibrous web layer. The fibrous web layer is maintained in a compressed state by the superabsorbent material, whereupon wetting of the absorbent matrix wets the superabsorbent material so that the fibrous web layer expands from its compressed state due to the inherent resilience of the layer, thereby facilitating swelling of the superabsorbent material. An absorbent panel so-configured is disclosed in U.S. Pat. Nos. 4,500,315, 4,537,590, and 4,573,988, which are incorporated herein by reference.

In the most preferred form, the absorbent matrix further includes liquid transport means comprising at least one wicking layer of densified hydrophilic fibers, typically densified wood pulp fibers. The wicking layer is coextensive with at least a portion of a respective expansive surface of the compressed fibrous web layer, and thus promotes liquid transport within the absorbent matrix to maximize utilization of the absorptive capacity of the fibrous web layer and the associated superabsorbent material.

As discussed above, it is typically necessary that the cross-sectional bulk of a diaper be accommodated between the thighs of a wearer by folding or corrugation of the diaper's absorbent panel. Experience has shown that when the diaper is fitted with one or more elastic elements at each of its leg openings for conforming the diaper to the wearer, it is the distance between the innermost elastic elements, as measured across the absorbent panel, that determines the width of the diaper which must be accommodated in the space between the wearer's thighs by folding or corrugating. To this end, the present diaper has been configured such that the minimum dimension between the opposite, innermost ones of such elastic elements at the impact zone of the diaper is no more than about 1.25 times the minimum transverse dimension of the absorbent panel of the impact zone. This relationship has been found to desirably minimize the bulk of the material which must be accommodated, while at the same time maintaining the design functionality of the diaper as it relates to waste containment.

Other features and advantages of the present invention will become readily apparent from the following detailed description, the accompanying drawings, and the appended claims.

DETAILED DESCRIPTION

While the present invention is susceptible of embodiment in various forms, there is shown in the drawings and will hereinafter be described presently preferred embodiments of the invention, with the understanding that the present disclosure is to be considered as an exemplification of the invention, and is not intended to limit the invention to the specific embodiments illustrated.

As used in the present disclosure, the term diaper is intended to refer to an absorbent article which is worn by an individual for absorbing urine and/or fecal matter. It is to be understood that diapers embodying the principles of the present invention can be appropriately sized for use by infants or babies, and can further be sized for use by incontinent adults. It will be further understood that absorbent articles other than disposable diapers can be provided with an absorbent unit or structure embodying the principles of the present invention. Such articles can include sanitary napkins, tampons, incontinent pads, wound dressings, absorbent wipes, and the like.

Figures 1, 2:
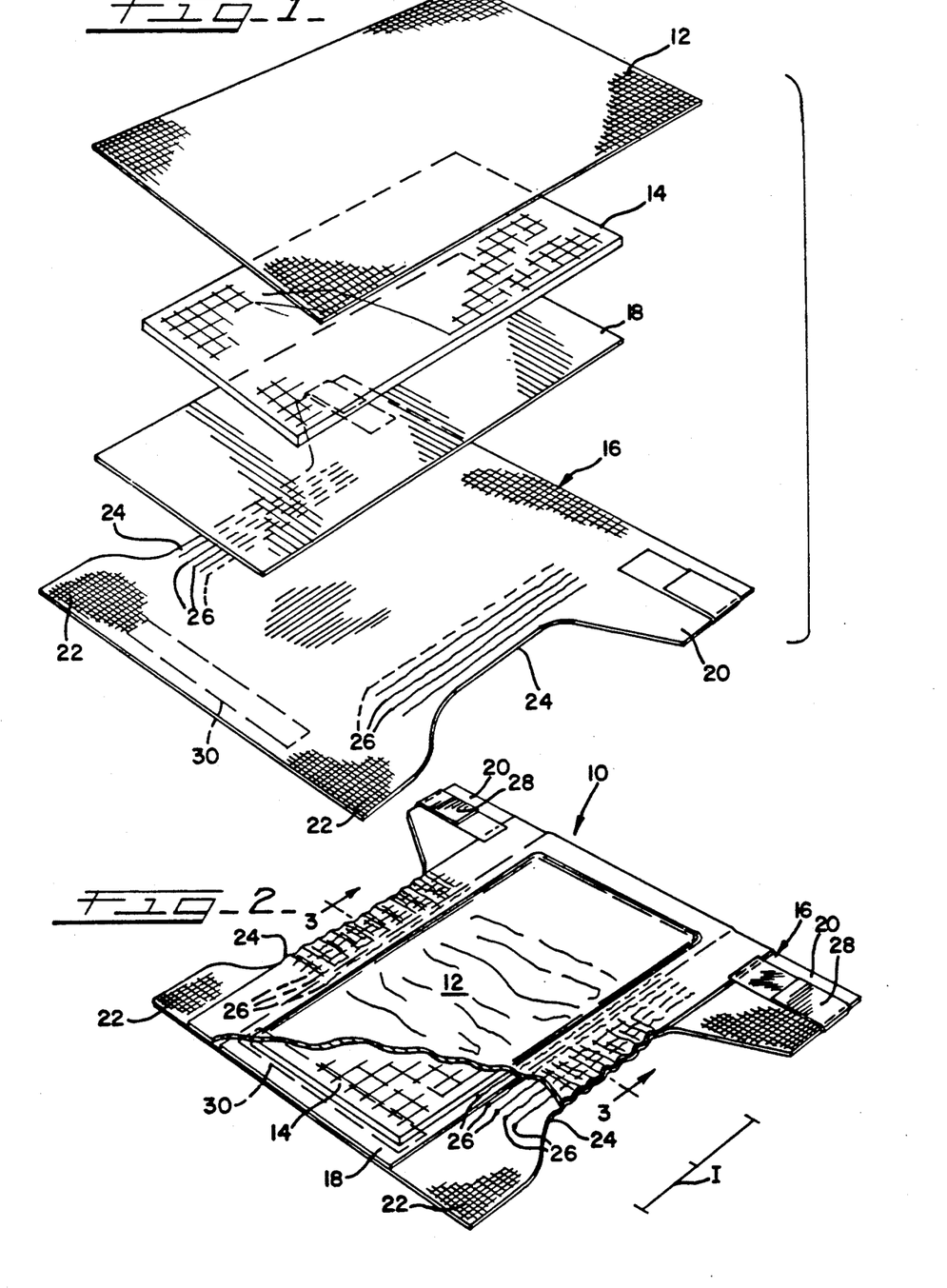
FIG. 1 is an exploded perspective view of a disposable diaper embodying the principles of the present invention.
FIG. 2 is a perspective view, partially cut-away, of the present disposable diaper.

Referring now to the drawings, therein is illustrated a disposable diaper 10 embodying the principles of the present invention. Diaper 10 includes a facing layer or topsheet 12 formed of moisture pervious material, with the facing layer being adapted for positioning adjacent to the wearer of the diaper. The diaper further includes an absorbent panel 14, which in the illustrated embodiment, is generally rectangular, but which may be otherwise shaped, such as T-shaped, I-shaped, hourglass-shaped, or otherwise contoured As will be further described, absorbent panel 14 preferably comprises an absorbent matrix of a resilient fibrous web with hydrocolloid or superabsorbent material distributed therein, with an associated wicking layer of densified cellulosic fibers provided on one or both of the expansive surfaces of the fibrous web for enhancing liquid transport within the absorbent matrix.

Disposable diaper 10 further includes a backing layer 16 positioned on the side of the absorbent panel 14 which is opposite the facing layer 12. While the backing layer may comprise moisture-impervious material, such as plastic film or sheet, it is presently preferred that the backing layer 16 comprise a moisture-pervious material, such as a non-woven fabric as used for facing layer 12, except backing layer 16 is preferably more hydrophobic than the facing layer to repel urine. If desired, the non-woven fabric used for the backing layer 16 is not treated with a surfactant compound in order to maintain the typical hydrophobicity of the fabric. In order to obviate passage of liquid from absorbent panel 14 through pervious backing layer 16, a moisture-impervious barrier layer 18 is preferably provided so that it underlies the absorbent panel, but is positioned inwardly of the backing layer 16.

A suitable material for the barrier layer 18 is an opaque polyolefin, for example, polyethylene about 0.0005–0.001 inches thick. Another suitable material for this purpose is polyethylene terephthalate having a thickness of about 0.0005–0.001 inches. Additionally, coatings of liquid impervious material, such as hot-melt adhesives, or hydrophobic coatings of silicone or flurocarbon compounds, can be applied to the layer 16 to provide the desired barrier properties.

The preferred relative dimensioning of the barrier layer 18 and the backing layer 16 should be noted. In particular, it is preferred that the barrier layer have a surface area which is less than the surface area of the backing layer, most preferably with the surface area of the barrier layer being no more than about 75 percent of the surface area of the backing layer. By this construction, breathability of the diaper is enhanced, thereby helping to avoid discomfort for the wearer by minimizing occlusion of the diaper. Additionally, this construction positions the preferably non-woven backing layer 16 at the exterior of the diaper, with its cloth-like texture desirably lending aesthetic appeal to the construction.

As will be recognized by those familiar with the art, several different types of facing materials may be used for facing layer 12, as well as for the moisture-pervious backing layer 16. For example, these layers may comprise a non-woven web made of a mixture of fibers consisting predominantly of inexpensive, short, cellulosic fibers such as wood pulp fibers or cotton linters in amounts of about 75 percent to 98 percent, with the balance being textile length fibers such as rayon as described in U.S. Pat. No. 3,663,348, to Liloia, et al. The non-woven fabrics may also be formed from polyester, polyethylene, polypropylene, nylon, rayon, or the like.

Non-woven materials for the facing layer 12 of the present diaper can have fabric weights in the range of from about 0.3 to 5 ounces per square yard and densities of less than 0.2 grams/cc, generally in the range of 0.05 to about 0.1 grams/cc. The dry strength of the facing sheet material for a fabric having a weight of about 1.5 ounces per square yard is at least 0.15 pounds per inch of width, in the machine direction, and at least 0.1 pound per inch of width in the cross direction. Such fabrics have good elongation, loft, softness, and drape characteristics.

Facing layer 12 and backing layer 16 may also be made of an apertured non-woven fabric which is formed, for example, in accordance with the teachings of U.S. Pat. Nos. 2,862,251, 3,081,514, and 3,081,515. Furthermore, these layers may also be made from other types of fabrics such as those disclosed and described in U.S. Pat. No. 3,485,706, to Evans. Such fabrics can be made of naturally occurring fibers, synthetic fibers, or blends thereof. Typical facing sheets made of polypropylene type fibers may have a weight of about 0.7 ounces per square yard.

In addition, the facing layer and backing layer of the present construction may be made from non-apertured materials such as non-woven isotropic webs or apertured polyolefin or polyester films having the desired moisture permeability. Spun-bonded and melt-blown fabrics can also be employed. In all of the aforementioned materials, the materials should be relatively hydrophobic so as to retard wicking within the material.

Referring again to the drawings, it is presently preferred that facing layer 12, absorbent panel 14, and barrier layer 18 all be of a rectangular configuration, while backing layer 16 be of a generally I-shaped, contoured configuration for the desired fit. Specifically, the backing layer 16 includes a pair of rearward ear portions 20, and a pair of forward ear portions 22, between which are defined a pair of generally cut-out leg openings 24.

The desired fit and leakage-resistant characteristics for the present disposable diaper are achieved by providing each leg opening 24 with one or more associated elastic elements whereby a gathering or contracting force is created at the leg openings so that the diaper conforms to and follows the movements of the wearer's legs. For purposes of the present discussion, reference to elastic members or the like is intended to encompass elastic materials, pre-stretched monofilament strands, polyurethane films or foams, elastomeric films, shrink film and other materials and structures which can be arranged to exert a gathering force on the associated diaper components. As used herein, the term "elastic" refers to sheets, films, ribbons, strands, elastic hot melt adhesives, elastomeric foams and nettings and the like which preferably have a recovery of at least 50 percent, when elongated at least 10 percent of their yield point, and measured in accordance with the following formula:

$$\text{Percent retraction} = \frac{(L_e - L_t)}{(L_e - L_o)} \times 100$$

where
 $L_o$=original length of sample
 $L_e$=fully extended length
 $L_t$=length of sample measured three seconds after released from extended length.

The thickness of monofilament elastic members is generally 10 mils or less. The thickness of elastic film material is typically about 0.5 to 2.0 mils. Elastomeric foam materials typically have a thickness of 1-2 mm. The elastic members have an extensibility to rupture of at least about 150 percent, and a recovery at 50 percent elongation of at least about 50 percent, and preferably at least about 75 percent.

In the illustrated embodiment of the present diaper, each leg opening 24 is provided with a plurality of generally parallel, elastic members 26 which cooperate to provide the desired sealing or gasketing effect at the leg opening, without applying undue force to the wearer of the diaper. Elastic elements 26 may be adhesively secured in position, or otherwise secured, such as ultrasonically, as is known in the art.

As will be further discussed, specific dimensional configurations of the present disposable diaper have been selected to enhance its desired conformity and fit, and wearer comfort. In this regard, it has been determined that the distance between the innermost ones of elastic elements 26 bears directly on the fit characteristics of the diaper.

Figure 3:
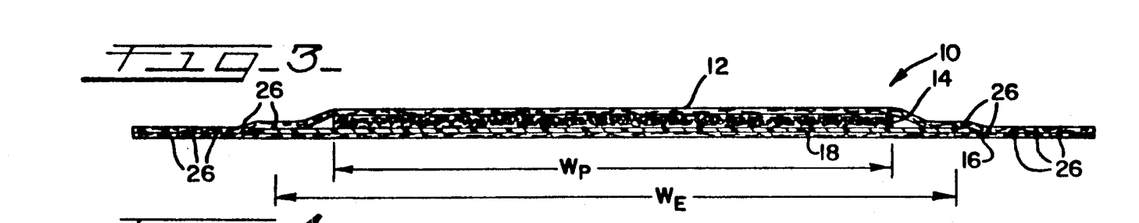
FIG. 3 is a cross-sectional view taken along lines 3—3 of FIG. 2.

Experience has shown that during wearing of the diaper, the innermost stretch elements will be located, for the most part, in the fold of the groin of the infant while the other stretch elements and the sides of the diaper fold onto the infant's upper thigh. Therefore, the distance between the innermost stretch elements, measured across the absorbent panel, determines the width of the diaper which must be accommodated in the space between the thighs by folding or corrugating. If this distance is relatively large, excessive bagging or hanging of the diaper between the infant's thighs will occur. For a diaper to exhibit the desired fit, the distance between the innermost stretch elements should be minimized, while still maintaining design functionality as it relates to waste containment. In this regard, it has been determined that the minimum distance between the innermost elastic elements, $W_E$ as shown in FIG. 3, should be no more than about 1.25 times the width $W_P$ of the associated absorbent panel 14.

In accordance with the above preferred dimensioning, the minimum dimension between the opposite, innermost ones of the elastic elements 26 of diaper 10 is preferably less than the minimum transverse dimension of the moisture impervious barrier layer 18, with the innermost elastic elements 26 positioned on top of the barrier layer 18 in the illustrated embodiment.

The superposed, multiple layers of the disposable diaper 10 may be secured together by any manner of known bonding techniques, including use of adhesives in the form of glue lines or sprays, and/or by ultrasonic bonding. When assembled in a typical fashion, barrier layer 18 is secured to backing layer 16, with absorbent panel 14 in turn then secured to the barrier layer. Facing layer 12 is superposed on the absorbent panel, and is secured, typically with glue lines, to the backing layer 16, barrier layer 18, and to the absorbent panel 14. For example, as shown in FIG. 3 of U.S. Pat. No. 4,573,988, which as set forth above, is incorporated herein by reference, glue lines are illustrated which secure the absorbent panel to the outer backing sheet, including at the waist portions of the diaper.

As shown in FIG. 2, disposable diaper 10 is generally in position for fitting to a wearer (although in FIG. 2, for purposes of clarity, the product has been shown substantially stretched in opposition to elastic members 26). With the diaper in a position generally as shown, a baby is placed face up on the diaper. The forward portion of the diaper having ear portions 22 is brought up between the baby's legs to a position covering the perineum and contiguous with the front portion of the baby's waist. The diaper is thereafter secured to the baby by bringing the rearward ear portions 20 around the baby into overlapping relation with the forward ear portions 22.

In order to secure the diaper in position, adhesive tape fasteners 28, as are well known in the art, are provided on the rearward ear portions 20. Each of these fasteners 28 include a tab-like element having pressure-sensitive adhesive thereon which, when brought into contact with the forward, outer waist portion of the diaper, secures the diaper in position. To this end, the outer forward waist portion of the diaper is preferably provided with a fastener-receiving strip 30 (sometimes referred to as a "target tape" or a "tape landing zone") to which the adhesive fasteners 28 are respectively secured.

The use of the fastener-receiving strip 30, which typically comprises a strip of plastic film adhesively secured to backing layer 16, is preferred for a variety of reasons. First of all, the use of strip 30 assists in the correct positioning of the tape fasteners 28 for achieving the desired fit of the diaper. Additionally, the strip 30 can be configured to cooperate with the adhesive of the tape fasteners 28 to provide a secure, yet releasable adhesive bond; a mother can thereby easily check to see whether a diaper needs changing.

Further, the strip 30 desirably acts to reinforce the forward portion of the diaper, thus facilitating the above opening and resealing without rupture of the diaper backing layer; this is a particularly desirable feature when the backing layer 16 is made from plastic film material. When the backing layer 16 is made from a breathable non-woven fabric as is presently preferred, the provision of strip 30 further desirably functions to provide the desired adhesive coaction with tape fasteners 28, which is desirable since the fibrous nature of a non-woven backing layer does not lend itself to secure bonding with adhesives such as typically used for tape fasteners 28.

Figure 6:
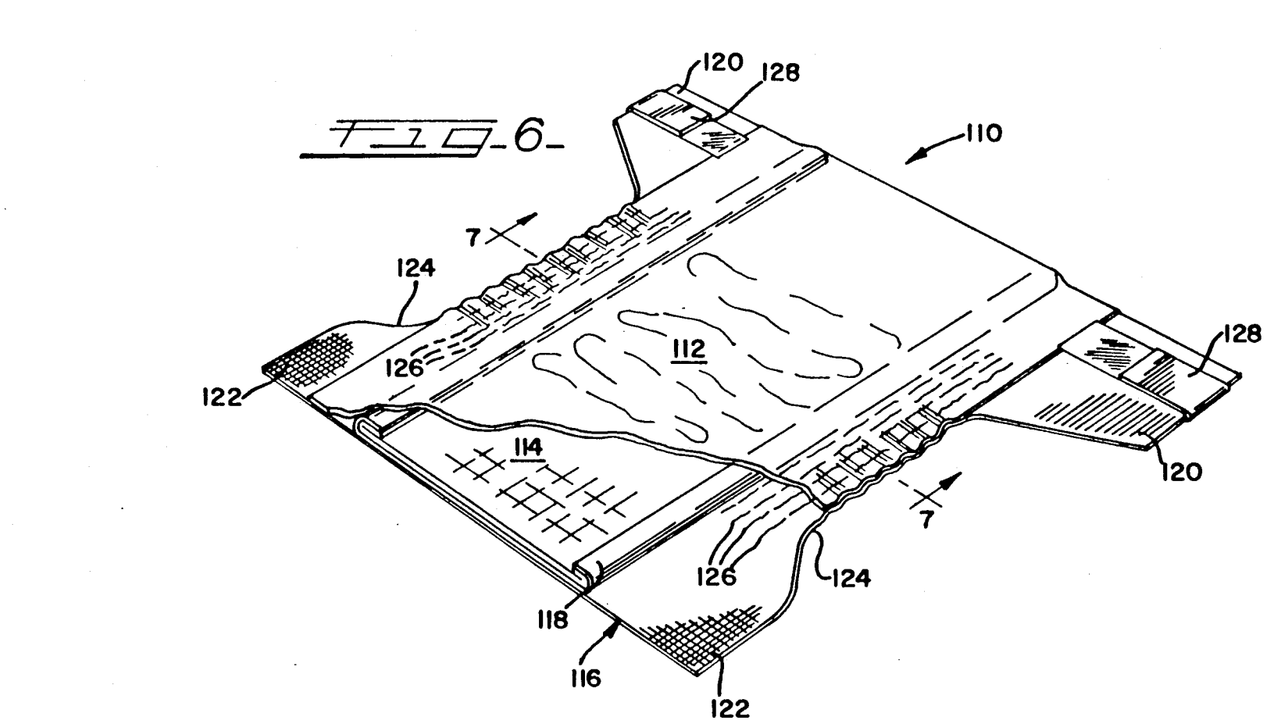
FIG. 6 is a perspective view, partially cut-away, of an alternate embodiment of the present disposable diaper.
Figure 7:
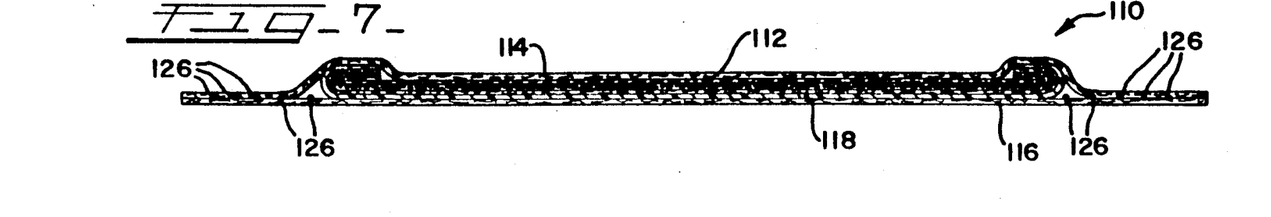
FIG. 7 is a cross-sectional view taken along lines 7—7 of FIG. 6.

Referring now to FIGS. 6 and 7, therein is illustrated an alternate embodiment of the present low bulk disposable diaper, designated 110. In most respects, the various elements of diaper 110 function in a manner similar to those elements in the previously-described embodiment 10, and such like elements are designated by like reference numerals in the one hundred-series.

Accordingly, the disposable diaper 110 comprises a topsheet or facing layer 112, preferably of moisture-pervious non-woven fabric, which is superposed on an absorbent panel 114. The absorbent panel 114 is positioned atop of a backing layer 116, preferably also comprising a non-woven fabric, with a moisture-impervious barrier layer 118 positioned between the absorbent panel and the backing layer.

In distinction from the previous embodiment, the opposite lateral edges of barrier layer 118 are folded inwardly over the opposite lateral edges of absorbent panel 114, with the opposite lateral edges of the absorbent panel also folded inwardly in the illustrated embodiment. This alternate construction can enhance containment of waste material generally upon and within the absorbent panel 114, thus obviating leakage of the diaper, while at the same time promoting diaper breathability by relatively increasing the surface area of the breathable backing layer 116 which is not covered by the impervious barrier layer 118.

As in the previous embodiment, backing layer 116 is of a contoured configuration, including rearward ear portions 120, and forward ear portions 122, between which are defined a pair of leg openings 124. A plurality of elastic elements 126 are provided in operative association with each of the leg openings 124, and as will be observed in the cross-sectional view of FIG. 7, the innermost ones of the elastic elements 126 are positioned from each other a distance which is no more than about 1.25 times the transverse dimension of the absorbent panel 114. Adhesive tape fasteners 128 are respectively provided on the rear ear portions 120 for securing the diaper in position on a wearer.

In developing the present invention, extensive testing was performed so as to optimize the preferred dimensional configuration of the present diaper, with like testing performed on a wide variety of commercial disposable diaper products. It is believed that these test results, as reported below, highlight the novel combination of fit and absorptive characteristics which are achieved with the present construction, enhancing the comfort provided during wearing of the diaper, yet without compromise of the absorptive and leakage-resistant characteristics for the construction.

The tested embodiment of the present low bulk diaper (designated LBD in the test data) was configured in accordance with the illustrated embodiment of FIGS. 1-3. In this regard, the test samples included an absorbent panel in accordance with the preferred embodiment of the invention, and which is disclosed in U.S. Pat. Nos. 4,500,315, 4,537,590, and 4,573,998, and which panel can be formed in accordance with the method of U.S. Pat. No. 4,540,454, all to Pieniak, et al., and all of which are incorporated herein by reference. This absorbent panel comprises an absorbent matrix of a substantially high loft, resilient fibrous web layer, with superabsorbent material distributed within the fibrous web layer. The superabsorbent material is preferably in the form of a plurality of particles or globules of superabsorbent disposed in a random and intermittent arrangement throughout the fibrous web. The particles or globules are of a size and spacing so that they do not interfere with the absorption of liquid by adjacent particles.

Notably, the fibrous web layer is maintained in a compressed state by the superabsorbent material, after undergoing compression during manufacture of the panel. By this arrangement, wetting of the absorbent matrix wets the superabsorbent material, so that the fibrous web layer expands from its compressed state due to the inherent resilience of the fibrous material. This facilitates swelling of the superabsorbent material without interference with adjacent particles or globules of the material.

In the preferred form, the absorbent matrix of the panel further includes liquid transport means in operative association with the absorbent fibrous web. The transport mechanism comprises at least one wicking layer of densified hydrophilic fibers, with the wicking layer being coextensive with at least a portion of a respective expansive surface of the fibrous web layer of the absorbent matrix. Notably, this arrangement has been found to provide a very efficient absorbent structure, in that the densified wicking layer promotes liquid transport from a point of introduction to various portions of the associated fibrous web and superabsorbent. One of the problems typically encountered in employing superabsorbent materials in absorbent articles is the fact that such superabsorbents typically do not transport or wick liquid effectively, but rather can exhibit "gel blocking" upon wetting which can inhibit liquid transport through the material. Thus, the wicking layer of the absorbent matrix desirably promotes liquid transport for efficient utilization of the superabsorbent.

In the low bulk diapers used for generating the following test data, an absorbent matrix in accordance with the above patents was employed having a density of 0.26 grams/cc, and a mean thickness of 0.13 inches. The above-described wicking layer is provided on each side of the compressed fibrous web of the structure, thus enhancing liquid transport. It is presently preferred that the superabsorbent material provided in the absorbent matrix comprise 200 to 1500 percent, by dry weight basis, of the fibrous material in the fibrous web, with the superabsorbent in the samples tested comprising about 1,000 percent add-on, by dry basis weight.

The absorbent composite is made by four steps. First, a structure is made by blending polyester fiber T-375W manufactured by DuPont and BICO 1040 fiber, made by BASF, in a ratio of 67/33%. this blend is carded into a high bulk non-woven web structure of approximately 1.20 oz/yd² weight and passed through an air bonder at a temperature of 325° F. for a duration of 5.6 seconds and at a pressure differential of 0.25 inches of water. This heat process bonds the web by melting the BICO fiber.

The second step consists of applying a coating of potassium acrylate solution at a consistency of 65% solids and 60% neutralized. The monoxer is added by suction coating to a level of 12.0 oz/yd² of dry coating weight. The coating is polymerized and cross-linked into a superabsorbent polymer by multiple electron beam irradiations of 2MRAD, 2MRAD, 8MRAD, 8MRAD, 8MRAD with an ESI 300 KV electron accelerator.

Pulp wicking layers are attached as the third step. Prior to this, the polymer was adjusted to 25% moisture content. It is passed through the suction zone of a Hammermill where pulp is defiberized and deposited at a weight of 4.8 oz/yd². Pulp is applied to the other side similarly and the entire composite is lightly sprayed with water and compressed to a thickness of 0.143 inches.

The fourth step consists of drying the composite in a rotary thru air dryer at 400° F. until it has a moisture content of less than 10%. It is softened by passing through embossing rolls as described in U.S. Pat. No. 4,605,402.

For comparison purposes, a number of different commercially available disposable diaper products were tested, with these designated Samples A-Q in the following test data. Between 10 and 20 individual samples were measured for generating the following data, with the arithmetic mean of data collected from like samples set forth in the following tables.

TABLE I

| Diaper Type | Diaper Thickness In Crotch Inches | Panel Width Inches | Cross Sectional Bulk (Panel Width × Thickness) Sq. Inches |
| --- | --- | --- | --- |
| Sample LBD | .13 | 4.5 | 0.585 |
| Sample A | .15 | 6.0 | 0.900 |
| Sample B | .21 | 5.188 | 1.089 |
| Sample C | .22 | 5.51 | 1.210 |
| Sample D | .25 | 5.24 | 1.313 |
| Sample E | .27 | 5.125 | 1.384 |
| Sample F | .27 | 5.0 | 1.350 |
| Sample G | .28 | 5.875 | 1.610 |
| Sample H | .31 | 5.0 | 1.550 |
| Sample I | .35 | 6.625 | 2.319 |
| Sample J | .40 | 5.0 | 2.000 |
| Sample K | .40 | 5.59 | 2.200 |
| Sample L | .43 | 5.0 | 2.150 |
| Sample M | .44 | 5.25 | 2.220 |
| Sample N | .45 | 6.875 | 3.094 |
| Sample O | .45 | 4.125 | 1.856 |
| Sample P | .46 | 3.75 | 1.725 |
| Sample Q | .63 | 6.75 | 4.253 |

Referring first to Table I, the thickness of the absorbent panels of the various samples, (measured at 0.5 psi) and the panel widths, measured at the center of the panel, are set forth. Table I further sets forth the resultant cross-sectional bulk of each panel sample, which directly relates to the comfort or discomfort of a disposable diaper.

Specifically, a measure of comfort can be determined by comparing the cross-section of a diaper crotch area in relation to the distance between the upper thighs of infants. In order for a relatively wide diaper of a certain panel thickness and width to fit between the infant's legs, the diaper, and specifically the panel, has to fold and/or corrugate. The extent to which the diaper cross-section (cross-sectional diaper bulk) exceeds the distance between the infant's legs is a measure of discomfort.

Attendant to testing, the distance between the legs of male and female infants, in the crotch area, was measured. It was found that the most common range for infants between 16-24 pounds and 9-18 months was between 0.0 and 1.0 inches, with a mean of 0.46 inches.

Referring again to Table I, it will be noted that the present low bulk diaper is clearly the thinnest one of the samples tested, and is substantially thinner than a number of the samples. This suggests that the present low bulk diaper will be the least bulky when worn.

TABLE II

Cross-Sectional Diaper Thickness When Diaper Is Folded To Fit Between Crotch

| Diaper Type | Panel Thicknesses: | | | |
|---|---|---|---|---|
| | ×2 Inches | ×4 Inches | ×6 Inches | ×8 Inches |
| Sample LBD | 0.26 | 0.52 | 0.78 | 1.04 |
| Sample A | 0.30 | 0.60 | 0.90 | 1.20 |
| Sample B | 0.42 | 0.84 | 1.26 | 1.68 |
| Sample C | 0.44 | 0.88 | 1.32 | 1.76 |
| Sample D | 0.50 | 1.00 | 1.50 | 2.00 |
| Sample E | 0.54 | 1.08 | 1.62 | 2.16 |
| Sample F | 0.54 | 1.08 | 1.62 | 2.16 |
| Sample G | 0.56 | 1.12 | 1.68 | 2.24 |
| Sample H | 0.62 | 1.24 | 1.86 | 2.48 |
| Sample I | 0.70 | 1.40 | 2.10 | 2.80 |
| Sample J | 0.80 | 1.60 | 2.40 | 3.20 |
| Sample K | 0.80 | 1.60 | 2.40 | 3.20 |
| Sample L | 0.86 | 1.72 | 2.58 | 3.44 |
| Sample M | 0.88 | 1.76 | 2.64 | 3.52 |
| Sample N | 0.90 | 1.80 | 2.70 | 3.60 |
| Sample O | 0.90 | 1.80 | 2.70 | 3.60 |
| Sample P | 0.92 | 1.84 | 2.76 | 3.68 |
| Sample Q | 1.26 | 2.52 | 3.78 | 5.04 |

Referring now to Table II, the cross-sectional diaper width of the various samples tested is shown when the panel is folded once (twice the panel thickness) to four times (eight times the panel thickness). Folding of the diaper between twice (four times panel thickness) and three times (six times panel thickness) is very commonly observed when infants wear diapers. As will be observed from Table II, all of the diapers except the present low bulk diaper exceed by far the space (0.0 to 0.46 inches) provided for between the infant's thighs.

The differences between the fit characteristics of the various diaper samples can be expressed as a Diaper Compression Index. For a diaper that is folded twice between the infant's legs (i.e., four times panel thickness), this number indicates how much more width the diaper occupies between the legs than is available when the infant is naturally standing without the diaper. This number can be calculated as follows:

DIAPER COMPRESSION INDEX $$\frac{\text{Diaper Thickness When Corrugated Twice (4} \times \text{diaper thickness)}}{\text{Distance between infants thighs (without diaper)}}$$

Example:

$$\frac{\text{Diaper Thickness When corrugated Twice (4} \times \text{diaper thickness)}}{\text{Distance Between infant's thighs (without Diaper)}} = \frac{0.53 \text{ in.}}{0.46 \text{ in.}} = 1.13$$

The following Table III shows the Diaper Compression Index for the various samples tested. This Table indicates that the present low bulk diaper has a negligible effect in encumbering the infant, while the other diapers tested far exceed the space available between the infant's legs.

TABLE III

| Diaper Type | Diaper Compression Index |
|---|---|
| Sample LBD | 1.13 |
| Sample A | 1.30 |
| Sample B | 1.83 |
| Sample C | 1.91 |
| Sample D | 2.17 |
| Sample E | 2.35 |
| Sample F | 2.35 |
| Sample G | 2.43 |
| Sample H | 2.70 |
| Sample I | 3.04 |
| Sample J | 3.48 |
| Sample K | 3.48 |
| Sample L | 3.74 |
| Sample M | 3.83 |
| Sample N | 3.91 |
| Sample O | 3.91 |
| Sample P | 4.00 |
| Sample Q | 5.48 |

As will be appreciated, the above test data relates to multiples of panel/diaper thickness in relation to the distance between the infant's legs. Another consideration for diaper fit and comfort is panel width and diaper width. Consumers prefer a snug fitting diaper because of its aesthetically appealing appearance, and the ease with which outer clothing can be applied over the diaper. It is therefore undesirable for the diaper to hang or bag in a pouch-like manner between the infant's legs.

Accordingly, it is believed that a further, and perhaps better, expression of diaper bulk between the infant's legs is the cross-sectional area of the panel occupying the space between the legs (i.e., panel width multiplied by panel thickness). To this end, the diaper with the smallest cross-sectional area should be the least bulky and hence the most comfortable. As shown on Table I, the present low bulk diaper creates just slightly more than one-half as much cross-sectional bulk area (in square inches) between the infant's legs (0.585 square inches) compared to the next best product tested, Sample A (0.90 square inches). It will be noted that some of the samples are many times bulkier than the present low bulk diaper. It is presently preferred that a medium sized diaper (for infants between 12 and 24 pounds) have a cross-sectional bulk at that portion of the diaper absorbent panel that fits between the thighs of no more than about 0.6 square inches.

The significance of this data was verified during testing on infants wearing the present low bulk diaper, as well as a variety of the commercial test samples. Referring to Table IV, the distance between the legs of several infants was measured with the infants standing without diapers. The various samples listed in Table IV were then fitted to the infants, and the distance between their legs again measured. Arithmetic means for the distances, as well as the percent increases, are shown on Table IV.

TABLE IV

Percent Increase of Distance Between Infant's Thighs As Result of Wearing Diapers

| Distance Between Infant's Thighs (Without Diaper) | Percent Increase From Original Distance (While Wearing Diaper) | | | | | | | | |
|---|---|---|---|---|---|---|---|---|---|
| | Sample LBD | | Sample C | | Sample D | | Sample H | | Sample J |
| Inches | | | | | | | | | |
| 0.50 | 0.75 | 50% | 2.00 | 300% | 2.00 | 300% | 2.00 | 300% | 2.50 400% |
| 0.13 | 0.25 | 96% | 2.00 | 1500% | 2.50 | 1900% | 2.00 | 1500% | 2.75 2100% |

TABLE IV-continued
Percent Increase of Distance Between Infant's Thighs As Result of Wearing Diapers

| Distance Between Infant's Thighs | Percent Increase From Original Distance (While Wearing Diaper) | | | | | | | | | |
|---|---|---|---|---|---|---|---|---|---|---|
| (Without Diaper) | Sample LBD | | Sample C | | Sample D | | Sample H | | Sample J | |
| 1.00 | 1.00 | 0% | 2.75 | 175% | 3.00 | 200% | 3.00 | 200% | 2.50 | 150% |
| 0.75 | 1.13 | 50% | 2.50 | 233% | 3.25 | 333% | 3.50 | 367% | 2.25 | 200% |
| 0.25 | 0.50 | 100% | 3.00 | 1100% | 4.25 | 1600% | 2.50 | 900% | 2.00 | 700% |
| 0.13 | 0.75 | 500% | 2.50 | 1900% | 2.50 | 1900% | 2.50 | 1900% | 2.13 | 1600% |
| X̄ 0.46 | X̄ 0.73 | 133% | X̄ 2.92 | 1039% | X̄ 2.46 | 868% | X̄ 2.58 | 861% | X̄ 2.35 | 858% |
| Based on Mean Measurements | | | | | | | | | | |
| X̄ 0.46 | 59% | | 436% | | 536% | | 464% | | 414% | |

Figure 4:
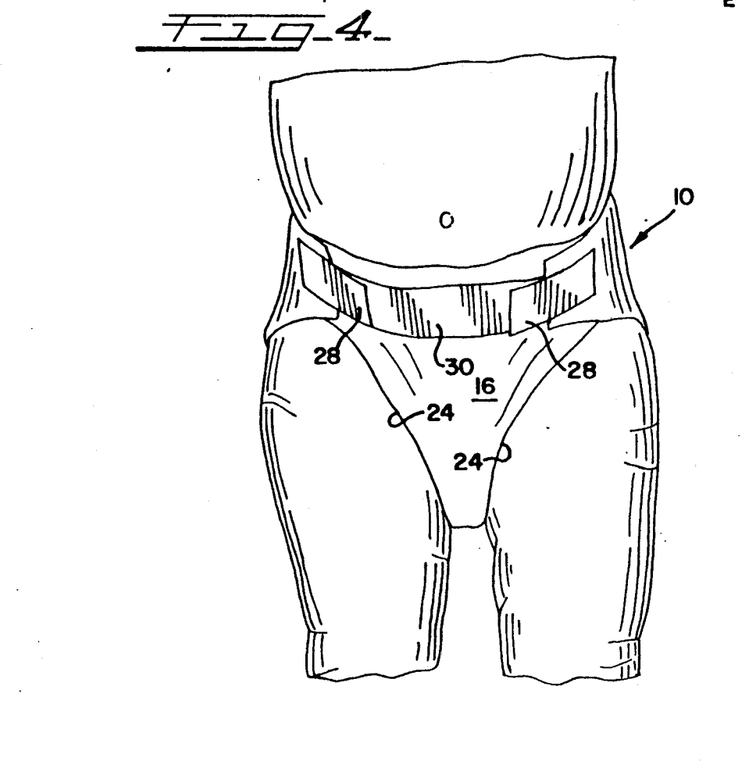
FIGS. 4 and 5 are illustrations made from photographs of an infant wearing a diaper embodying the principles of the present invention, and a conventional disposable diaper, respectively.
Figure 5:
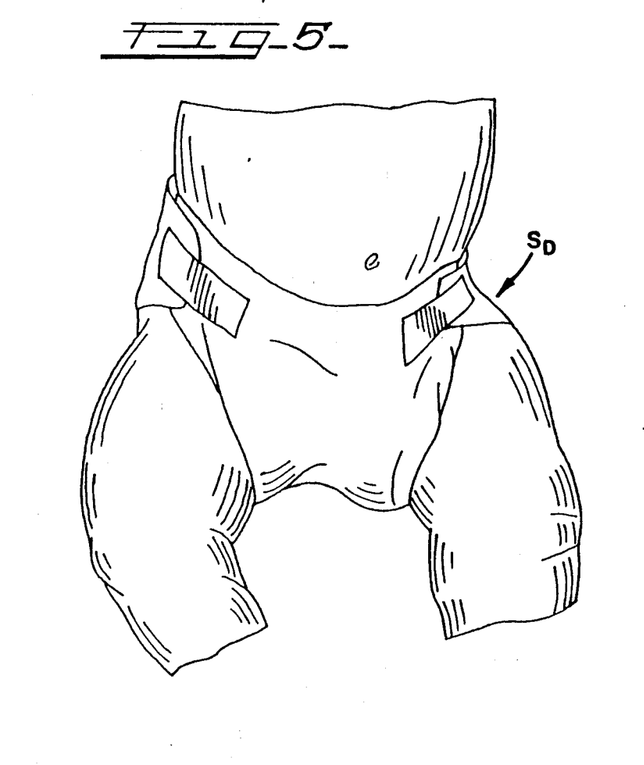

It is believed that the data in this table is particularly significant in ascertaining the comfort of diaper fitting. As will be observed, the present low bulk diaper exhibited a mean increase in the distance between the infants' legs of 59 percent. In comparison, the mean increases for the other samples tested varied from 414 percent to 536 percent. The significance of these numbers can be readily observed in FIGS. 4 and 5. These drawings were prepared from and closely correspond to photographs taken during the above testing. These drawings show the same infant (female, 18 months) for which the distance between the infant's thighs was measured at 0.13 inches when standing without a diaper. In FIG. 4, the infant is shown wearing the present low bulk diaper, with an increase of the distance between the legs being 0.62 inches. In marked contrast, the commercial product, Sample D, was fitted to the same infant, which resulted in the infant's legs being further spaced apart an increased distance of 2.37 inches.

Another manner in which the bulk differences between various diapers can be expressed in relation to the anatomy of infants is the Diaper Discomfort Factor. In this calculation, as shown below for the low bulk diaper, panel volume of the diaper impact zone (within the crotch region) is related to the distance between the infant's thighs without a diaper in a natural standing position. As designated I in FIG. 2, the impact zone is defined as the second and third fifths of the diaper absorbent panel, as measured from the front of the panel. Moisture-impervious barrier layer 18 of the illustrated embodiment is at least coextensive with this portion of the absorbent panel 14, and preferably coextensive with substantially the entire panel.

The length of the impact zone of the diaper where urination is most likely to occur is, for mid-size diapers (for infants 12-24 pounds) approximately 6 inches in length. Accordingly, the six inch dimension was used in calculation of the Discomfort Factor. Noting that the smaller the number, the smaller the discomfort for the infant, this factor for the present low bulk diaper is calculated as follows:

DISCOMFORT FACTOR $$\frac{\text{Crotch region panel bulk (i.e., panel width} \times \text{impact zone} \times \text{thickness)}}{\text{Distance between infants thighs (without diaper)}}$$

Example:

$$\frac{4\frac{1}{4}'' \times 6'' \times .13''}{0.46''} = \frac{57.5 \text{ cc}}{1.17 \text{ cm}} = 49.1 \text{ cm}^2$$

Note:

-continued

The smaller the number the smaller the discomfort for the infant.

The following Table V again shows that the present low bulk diaper results in significantly less discomfort for the wearer than other commercial diaper products.

TABLE V

| Diaper Type | Discomfort Factor |
|---|---|
| Sample LBD | 49.15 |
| Sample A | 75.63 |
| Sample B | 91.45 |
| Sample C | 101.82 |
| Sample D | 110.08 |
| Sample E | 116.24 |
| Sample F | 113.44 |
| Sample G | 138.23 |
| Sample H | 130.24 |
| Sample I | 194.82 |
| Sample J | 168.06 |
| Sample K | 187.82 |
| Sample L | 180.67 |
| Sample M | 194.11 |
| Sample N | 259.94 |
| Sample O | 155.88 |
| Sample P | 144.95 |
| Sample Q | 357.29 |

Another factor which determines the fit and comfort level of a diaper relates to the distance between the innermost elastic elements at the leg openings of the product. Elastic elements tend to contract or gather the side portions of the diaper in order for the diaper to conform snugly to the infant's body, specifically through the groin and along the upper thighs for the desired waste containment.

Experience has shown that the innermost ones of the elastic elements of a diaper will be located, for the most part, in the fold of the groin of the infant, with other elastic elements in the sides of the diaper folded onto the infant's upper thigh. It is therefore the distance between the innermost elastic members, measured across the absorbent panel, that determines the width of the diaper which has to be accommodated in the space between the thighs via folding or corrugating. As will be appreciated, if this distance is large, excessive bagging or hanging of the diaper between the infant's thighs will occur. Accordingly, it is desirable to minimize this distance, while still providing the desired waste containment characteristics.

A sample calculation for Diaper Fit Index is shown below, with the following Table VI showing values for the present low bulk diaper, as well as for the commercial products which were tested. As will be observed, this index is a ratio of the distance between the innermost elastic elements of a diaper product, measured across the diaper panel in the crotch area, and the distance between the upper thighs of infants.

DIAPER FIT INDEX

Example $$\frac{\text{Distance between innermost stretch members}}{\text{Distance between infants thighs (without diaper)}} = \frac{5\frac{1}{2}''}{0.46''} = 11.9$$

TABLE VI

| Diaper Type | Diaper Fit Index |
|---|---|
| Sample LBD | 12.52 |
| Sample A | 16.76 |
| Sample B | 16.54 |
| Sample C | 13.17 |
| Sample D | 16.80 |
| Sample E | 16.58 |
| Sample F | 17.41 |
| Sample G | 14.78 |
| Sample H | 16.43 |
| Sample I | 15.97 |
| Sample J | 16.45 |
| Sample K | 16.60 |
| Sample L | 16.36 |
| Sample M | 16.52 |
| Sample N | 16.02 |
| Sample O | 18.23 |
| Sample P | 18.15 |
| Sample Q | 15.86 |

As will be appreciated, due to the fact that the present low bulk diaper, when compared to other commercial products, has one of the narrowest diaper panels and the smallest distance between the innermost stretch elements of all of the commercially available diapers, it has the preferred Diaper Fit Index.

The final parameter of the present low bulk diaper relates to its absorptive characteristics, thus providing a diaper which provides improved fit and comfort, while at the same time providing enhanced absorptivity and leakage-resistance. As noted above, the parameters of diaper comfort and fit are associated with a thin, narrow pad, with the innermost elastic elements along each panel edge placed as close to the panel as feasible.

It has been determined that an appropriate standard in ascertaining functionality with respect to absorptive capacity is that the impact zone of the diaper be capable of absorbing about 220 cc of urine throughout its usage (this representing the 90th percentile of void volume for diapers during overnight usage). Approximately 60 percent of the urine introduced into the impact zone remains there while the other 40 percent distributes throughout the rest of the panel.

In order to combine the features of a thin and narrow panel with high absorptive capacity, the diaper panel in the impact zone has to be able to absorb anticipated volumes of voided liquid in a relatively small panel volume. The present low bulk diaper is designed in such a way that the panel bulk (i.e., the volume of the absorptive medium) in the crotch area (i.e., impact zone) is mimimized while the absorptive capacity in the impact zone is at the required level as to assure a low probability of diaper failure due to urine leakage.

The relationship between diaper bulk and absorptive capacity can be expressed as the Absorbency Efficiency Index. As shown below, this number is derived by dividing the urine volume at the 90th percentile level in the impact zone (of a mid-size diaper) by the volume of the impact zone absorptive medium. The impact zone is defined as before as the 6 inches of panel located at the second and third fifths of the panel length, as measured from the front of the diaper.

ABSORBENCY EFFICIENCY INDEX

Urine volume 90th percentile in overnight use: 220 cc.

Volume in crotch region approximately 60% of the total volume. Crotch area impact zone 6".

Crotch area impact zone is defined by the second and third fifths of the panel length measured from front end of diaper. This length is approximately 6 inches for mid-size disposable diapers.

Definition of panel bulk of impact zone in crotch area: panel volume of the 6 inch panel length (panel thickness measured at 0.5 psi).

Example:

$$\frac{220 \text{ cc} \times 0.6}{\text{bulk of crotch area}} = \frac{220 \text{ cc} \times 0.6}{4.5 \text{ in. (panel width)} \times 0.13 \text{ in. (Panel thickness)} \times 6 \text{ in. (impact zone length)} \times 16.39 \text{ cc/cu in.}} = 2.29$$

TABLE VII

| Diaper Type | Absorbency Efficiency Index |
|---|---|
| Sample LBD | 2.29 |
| Sample A | 1.49 |
| Sample B | 1.23 |
| Sample C | 1.11 |
| Sample D | 1.02 |
| Sample E | 0.97 |
| Sample F | 0.99 |
| Sample G | 0.81 |
| Sample H | 0.86 |
| Sample I | 0.58 |
| Sample J | 0.67 |
| Sample K | 0.60 |
| Sample L | 0.62 |
| Sample M | 0.58 |
| Sample N | 0.43 |
| Sample O | 0.72 |
| Sample P | 0.78 |
| Sample Q | 0.32 |

As clearly shown on the above Table VII, the present low bulk diaper design has by far the highest Absorbency Efficiency Index of the commercially available diapers tested. It is believed that this number is particularly significant, since it indicates that a diaper having improved fit and comfort characteristics can nevertheless be effectively made without compromising the desired absorbent characteristics of the product.

Summarizing, the disposable diaper embodying the principles of the present invention enhances the comfort for the wearer since the diaper can be worn without forcing a dramatic dislocation of the thighs and legs of an infant as is the usual case with currently available commercial products. Not only does this provide greater comfort, it is believed that the present diaper construction could provide pediatric benefits to the infants by avoiding artificial dislocation of the limbs.

Additionally, the present diaper is configured to provide high absorptive capacity in the impact zone while at the same time exhibiting low panel bulk, i.e., exhibits high absorbency efficiency. Additionally, the manner in which the present diaper is configured so that the innermost ones of the elastic elements of the leg openings are spaced as closely together provides a snug fit between the infant's legs, thus facilitating convenient consumer use.

From the foregoing, it will be observed that numerous modifications and variations can be effected without departing from the true spirit and scope of the novel concept of the present invention. It is to be understood that the present disclosure is to be considered as an exemplification of the invention, and is not intended to limit the invention to the specific embodiments illustrated. The disclosure is intended to cover by the appended claims all such modifications as fall within the scope of the claims.

What is claimed is:

1. A disposable diaper having improved fit and comfort, the diaper having front and back waist end portions and comprising:
   an absorbent panel;
   a moisture-pervious facing layer positioned in overlying relationship on one side of said absorbent panel, said facing layer being adapted for positioning adjacent the wearer of the diaper; and
   an outer backing layer positioned on the side of said absorbent panel opposite said facing layer;
   the absorbent panel and outer backing layer being secured together at the waist portions of the diaper;
   said absorbent panel comprising a matrix of absorbent material and having an impact zone which comprises the second and third fifths of said absorbent panel in a longitudinal direction as measured from the front thereof, said impact zone including a portion positionable between the thighs of the wearer, which said portion has a transverse dimension and a thickness dimension to provide a cross-sectional area for said portion of no more than about 0.6 square inches, said matrix of said absorbent panel having sufficient inherent absorbency to provide said absorbent with an absorbency efficiency index of at least 1.5, thereby providing sufficient absorbent capacity for absorbing anticipated volumes of voided liquid with a structure which is sufficiently narrow and thin so as to minimize discomfort to the wearer.

2. A disposable diaper in accordance with claim 1, including
   at least one elastic element positioned along each transverse marginal portion of said absorbent panel, the minimum dimension between opposite, innermost ones of said elastic elements at said impact zone being no more than about 1.25 times said minimum transverse dimension of said absorbent panel at said impact zone.

3. A disposable diaper in accordance with claim 1, including
   moisture-impervious barrier means secured to said backing layer and underlying and being secured to said absorbent panel, said barrier means having a surface area less than the surface area of said backing layer.

4. A disposable diaper in accordance with claim 3, wherein
   said barrier means comprises a substantially moisture-impervious barrier layer positioned between said absorbent panel and said backing layer, said backing layer comprising moisture-pervious material to thereby minimize the occlusion of said diaper.

5. A disposable diaper in accordance with claim 4, wherein
   said moisture impervious barrier layer includes opposite lateral edge portions folded over and in contact with respective opposite lateral edge portions of said absorbent panel, the opposite lateral edge portions of the barrier layer also being positioned in contact with overlying portions of the facing layer.

6. A disposable diaper in accordance with claim 4, including
   a plurality of elastic elements positioned along each transverse marginal portion of said absorbent panel, the minimum dimension between opposite, innermost ones of said elastic elements being less than the minimum transverse dimension of said moisture-impervious barrier layer.

7. A disposable diaper in accordance with claim 1, wherein
   said surface area of said barrier means is no more than about 75 percent of said surface area of said backing layer.

8. An absorbent panel in accordance with claim 1, wherein
   said absorbent matrix comprises a substantially high loft, resilient fibrous web layer, and superabsorbent material distributed within said fibrous web layer, said fibrous web layer being maintained in a compressed state by said superabsorbent material, whereupon wetting of said absorbent matrix wets said superabsorbent material so that said fibrous web layer expands from its compressed state due to the inherent resilience of said fibrous web layer, thereby facilitating swelling of said superabsorbent material.

9. An absorbent panel in accordance with claim 9, wherein
   said absorbent matrix further includes liquid transport means comprising at least one wicking layer of densified hydrophilic fibers, said wicking layer being coextensive with at least a portion of a respective expansive surface of said fibrous web layer to promote liquid transport within said absorbent matrix by said wicking layer.

10. A disposable diaper according to claim 1 in which the outer backing layer is of a liquid impermeable plastic film.

11. A disposable diaper according to claim 1 in which the said portion positionable between the thighs of the wearer has a transverse dimension of about 4.5 inches, a thickness dimension of about 0.13 inches and an absorbency efficiency index of about 2.29.

12. An absorbent panel for use in an absorbent article having a facing layer and a backing layer on respective opposite sides of said absorbent panel, said absorbent panel providing the absorbent article with improved comfort and fit for the wearer, said absorbent panel comprising:
   a matrix of absorbent material having sufficient inherent absorbency to provide a volumetric storage capacity of at least about 220 cc. of liquid, said absorbent panel having a bulk volume in a portion of the panel positionable between the thighs of the wearer, which said bulk volume is derived from said panel portion having a transverse dimension of about 4.5 inches and a thickness dimension of about 0.13 inches to provide a cross-sectional area for said portion of about 0.6 square inches, and to thereby provide said absorbent panel with an absorbency efficiency index of about 2.29, wherein said absorbent panel includes an impact zone comprising the second and third fifths of said absorbent in a longitudinal direction thereof, said impact zone including said portion of said panel, said absorbent matrix comprising superabsorbent material and fibrous material, said superabsorbent material comprising 200-1,500 percent, by dry weight basis of said fibrous material, said absorbent panel having a density of at least about 0.25 grams/cubic centimeters, whereby a sufficient absorbent capacity for absorbing anticipated volumes of voided liquid is provided by a structure which is sufficiently narrow and thin so as to minimize discomfort to the wearer.

13. An absorbent panel in accordance with claim 12, wherein
said transverse dimension of said portion of said absorbent panel is no more than about 40 times said thickness dimension thereof.

14. An absorbent panel in accordance with claim 12, wherein
said backing layer of said absorbent article comprises moisture-impervious material with said article including moisture-impervious barrier means at least coextensive with said impact zone of said absorbent panel, wherein the surface area of said moisture-impervious barrier means is no more than about 75 percent of the total surface area of said backing layer, to provide said absorbent article with improved breathability and comfort for the wearer.

15. An absorbent panel in accordance with claim 12, wherein
said absorbent article includes at least two elastic elements positioned along respective transverse marginal portions of said absorbent panel, the dimension between opposite, innermost ones of said elastic elements at said panel portion in said impact zone being no more than about 1.25 times said transverse dimension of said panel portion.

16. An absorbent panel in accordance with claim 12, wherein
said absorbent matrix comprises a substantially high loft, resilient fibrous web layer, and superabsorbent material distributed within said fibrous web layer, said fibrous web layer being maintained in a compressed state by said superabsorbent material, whereupon wetting of said absorbent matrix wets said superabsorbent material so that said fibrous web layer expands from its compressed state due to the inherent resilience of said fibrous web layer, thereby facilitating swelling of said superabsorbent material.

17. An absorbent panel in accordance with claim 16, wherein
said absorbent matrix further includes liquid transport means comprising at least one wicking layer of densified hydrophilic fibers, said wicking layer being coextensive with at least a portion of a respective expansive surface of said fibrous web layer to promote liquid transport within said absorbent matrix by said wicking layer.

* * * * *

UNITED STATES PATENT AND TRADEMARK OFFICE
CERTIFICATE OF CORRECTION

PATENT NO. : 5,098,423
DATED      : March 24, 1992
INVENTOR(S) : Heinz A. Pieniak and Gloria Huffman It is certified that error appears in the above-identified patent and that said Letters Patent is hereby corrected as shown below:

Column 9, line 48, "this" should be --This--;

Column 16, after the Example at lines 22-27, and before TABLE VII, insert:

--NOTE: The highest number denotes a diaper which absorbs the largest with the least panel volume--; and Column 18, line 37, "9," should be --8,--.

Signed and Sealed this

Third Day of August, 1993

Attest:

MICHAEL K. KIRK

Attesting Officer

Acting Commissioner of Patents and Trademarks